(12) United States Patent
Nordbryhn

(10) Patent No.: US 9,785,868 B2
(45) Date of Patent: Oct. 10, 2017

(54) REVERSE VENDING MACHINE AND METHOD OF DETECTING DIRT IN A REVERSE VENDING MACHINE

(75) Inventor: Andreas Nordbryhn, Oslo (NO)

(73) Assignee: TOMRA SYSTEMS ASA, Asker (NO)

( * ) Notice: Subject to any disclaimer, the term of this patent is extended or adjusted under 35 U.S.C. 154(b) by 497 days.

(21) Appl. No.: 14/128,944

(22) PCT Filed: Jun. 22, 2012

(86) PCT No.: PCT/NO2012/050115
§ 371 (c)(1),
(2), (4) Date: Apr. 7, 2014

(87) PCT Pub. No.: WO2012/177146
PCT Pub. Date: Dec. 27, 2012

(65) Prior Publication Data
US 2014/0218510 A1    Aug. 7, 2014

(30) Foreign Application Priority Data

Jun. 24, 2011    (EP) .................................... 11171367

(51) Int. Cl.
*H04N 7/18*    (2006.01)
*G06K 9/78*    (2006.01)
*G07F 7/06*    (2006.01)
*G01N 21/94*    (2006.01)

(52) U.S. Cl.
CPC .............. *G06K 9/78* (2013.01); *G01N 21/94* (2013.01); *G07F 7/0609* (2013.01); *H04N 7/18* (2013.01)

(58) Field of Classification Search
CPC ...................................................... G06K 9/78

USPC ......................................................... 348/131
See application file for complete search history.

(56) References Cited

U.S. PATENT DOCUMENTS

| 5,355,213 | A |   | 10/1994 | Dotan |
|---|---|---|---|---|
| 5,790,247 | A | * | 8/1998 | Henley ................ G01N 21/958 356/237.1 |
| 6,226,080 | B1 |   | 5/2001 | Takeuchi et al. |
| 7,211,771 | B1 |   | 5/2007 | Smith et al. |

(Continued)

FOREIGN PATENT DOCUMENTS

| GB | 1 395 113 A | 5/1975 |
|---|---|---|
| GB | 1 484 613 A | 9/1977 |

(Continued)

OTHER PUBLICATIONS

Examiner's report issued on May 28, 2015, in corresponding Australian Patent Application No. 2012273533. (2 pages).

(Continued)

*Primary Examiner* — Richard Torrente
(74) *Attorney, Agent, or Firm* — Buchanan Ingersoll & Rooney P.C.

(57) ABSTRACT

A reverse vending machine, including: a chamber adapted to receive an object returned to the reverse vending machine; a plurality of cameras arranged around the perimeter of the chamber for viewing said object; a transparent or translucent plate arranged such that the cameras in use view the object obliquely through the transparent or translucent plate; and means adapted to couple light into the plate such that the light undergoes total internal reflection in the plate. Also, a method of detecting dirt in a reverse vending machine.

14 Claims, 8 Drawing Sheets

(56) References Cited

U.S. PATENT DOCUMENTS

2007/0035954 A1    2/2007  Schanz et al.
2007/0165213 A1    7/2007  Fang et al.
2008/0094721 A1*   4/2008  Moss ..................... H04N 9/315
                                                        359/638
2010/0290767 A1*  11/2010  Lunde .................. G07F 7/0609
                                                        396/4

FOREIGN PATENT DOCUMENTS

WO    WO 2005/064321 A1   7/2005
WO    WO 2009/021515 A1   2/2009
WO    WO 2009/061207 A1   5/2009

OTHER PUBLICATIONS

International Search Report (PCT/ISA/210) mailed on Aug. 3, 2012, by the European Patent Office as the International Searching Authority for International Application No. PCT/NO2012/050115.
International Preliminary Report on Patentability (PCT/IPEA/409) mailed on May 22, 2013, by the European Patent Office as the International Searching Authority for International Application No. PCT/NO2012/050115.
European Search Report for EP 11171367 dated Oct. 28, 2011.
S. Igaki et al., "Real-Time Fingerprint Sensor Using a Hologram", Apr. 10, 1992, pp. 1794-1802, Applied Optics, vol. 31, Issue 11.
J. Paradiso, "Several Sensor Approaches that Retrofit Large Surfaces for Interactivity", Presented at the ACM Ubicomp 2002 Workshop on Collaboration with Interactive Walls and Tables, Sep. 29, 2002, 8 pages.

* cited by examiner

⇠-- = incoupled light 36

REVERSE VENDING MACHINE AND METHOD OF DETECTING DIRT IN A REVERSE VENDING MACHINE

FIELD OF USE

The present disclosure relates to a reverse vending machine (RVM). The present disclosure also relates to a method of detecting dirt in a reverse vending machine, in particular at places where the dirt may prevent the RVM's function.

BACKGROUND

Unrelated to RVMs, Igaki et al. "Real-time fingerprint sensor using a hologram" Applied Optics, Vol. 31, Issue 11, pp. 1794-1802 (1992) discloses a fingerprint sensor, wherein a beam is introduced into a prism from one of its slanted surfaces. This beam is arranged so as to meet the conditions for total internal reflection at the top surface of the prism. When a finger is placed on top of this surface, the conditions for total internal reflection are no longer met at the points of contact. Consequently light incident at these points will not be reflected and an image is created of the fingerprint. This image then passes out of the prism at the other slanted surface and is brought into focus on the image pickup element (charge-coupled device (CCD)) with the help of a lens system.

Also unrelated to RVMs, GB 1484613 discloses a windscreen soiling sensor comprises a light source emitting light through prism and windscreen so that it suffers total internal reflection from dirtiable surface, when it is clean, and, in the same housing, photometer sensing changes, due to windscreen soiling, of the light transmitted back through prism. The light is passed through focusing system and reflected from mirror and again focused by system, on to photometer, with iris, supplying a signal circuit which may, if the change exceeds a limit, switch on a windscreen cleaner.

Bonding has the same refractive index as the adjacent components.

Also unrelated to RVMs, GB1395113 discloses an apparatus for detecting obscuring matter, e.g. dirt, condensation, on a lamp glass or windscreen of a vehicle. The apparatus comprises means for directing a modulated optical or infrared beam on to the screen or glass and means for detecting correspondingly modulated radiation back-scattered from the screen by obscuring matter. A light-emitting diode, a photodetector and a control circuit are provided. A further embodiment utilizes the effective change in total internal reflection caused by back-scattering resulting from contamination. In this mode light is directed into the edge of the glass.

SUMMARY

According to an aspect of the present disclosure, there is provided a reverse vending machine, comprising: an interior adapted to receive an object returned to the reverse vending machine; a plurality of cameras arranged around the perimeter of the interior for viewing said object; a transparent or translucent plate arranged such that the cameras in use view the object obliquely through the transparent or translucent plate; and means adapted to couple light into the plate such that the light undergoes total internal reflection in the plate.

Said means may be arranged to couple light into the plate in directions that are generally opposite the respective cameras' viewing directions through the plate.

The plate may have an opening corresponding to the perimeter of the chamber, wherein said means are positioned around said opening.

Said means may be provided externally to the transparent or translucent plate.

Said means may be provided on the same side of the transparent or translucent plate as the cameras.

Said means may include at least one light source with an associated prism. The prism may be on the transparent or translucent plate, wherein the light source is adapted to emit light that in use is coupled into the transparent or translucent plate via the associated prism. The prism may be triangular. Alternatively, the prism may have a first surface for receiving light from the light source, at least one second surface which is reflective, and a third surface facing the plate, wherein the at least one second surface is arranged to receive light in-coupled through the first surface and reflect it towards the third surface.

Said means may include at least one light source with an associated diffuser which is on the transparent or translucent plate.

Said means may include one or more light sources arranged at an edge of the transparent or translucent plate for directing light into the edge of the plate.

Said cameras may be configured to detect any dirt or other obscuring matter on the plate when said means are activated.

The reverse vending machine may further comprise a controller connected to said means for manual and/or automatic activation of said means.

According to another aspect of the present disclosure, there is provided a method of detecting dirt or other obscuring matter in a reverse vending machine as described above, which method comprises: manually or automatically activating said means for coupling light into the transparent or translucent plate; and viewing at least a portion or portions of said plate using said cameras while light is coupled into the plate using said means for detecting any dirt or other obscuring matter on said plate. This aspect of the disclosure may exhibit the same or similar features and technical effects as the previously described aspect.

BRIEF DESCRIPTION OF THE DRAWINGS

The present disclosure will now be described in more detail, with reference to the appended drawings showing currently preferred embodiments of the disclosure.

DETAILED DESCRIPTION

A reverse vending machine (RMV) 10 according to one or more embodiments of the present disclosure will now be described initially with reference to FIGS. 1 and 2.

Generally, the RVM 10 is adapted to receive returnable objects, for instance empty containers such as bottles and/or cans, and to provide remuneration for the returned objects to the person returning the objects. The remuneration may for instance be in the form of cash or a voucher.

The RVM 10 has a front 12 and a back 14. The interior of the RVM includes a chamber 16 which may extend from the front 12 towards the back 14. The chamber 16 is adapted to receive an object 18 returned to the RVM 10, e.g. an empty bottle or a can. The typical transportation direction for the object 18 through the chamber 16 is illustrated by the arrow in FIG. 1.

Figure 11:
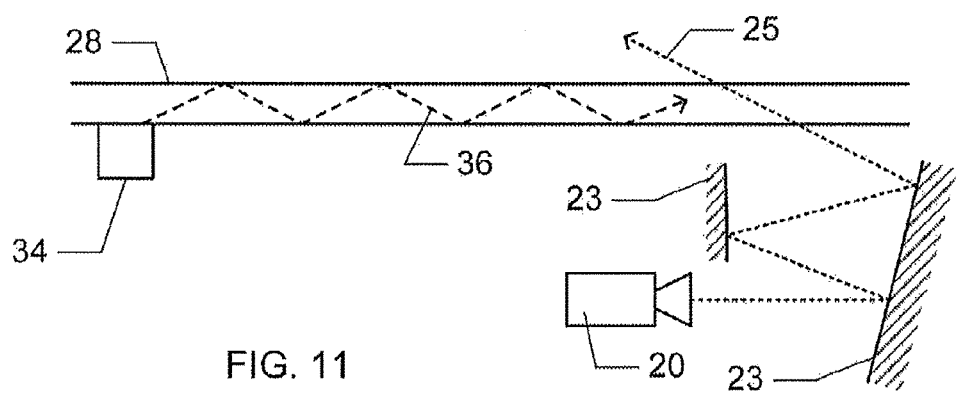
FIG. 11 is a partial side view of an RVM according to an embodiment of the present disclosure.

The RVM 10 further comprises a plurality of cameras or imaging devices 20 arranged outside and around a perimeter 22 of the chamber 16. The cameras 20 are preferably evenly distributed the perimeter (or circumference) 22. The number of cameras 20 may for instance be six. The cameras 20 are typically digital video cameras. The cameras 20 are aimed to at least partly view the object 18 in the chamber 16 when the object 18 is its position shown in FIG. 1, either directly as in FIG. 1, or via some reflecting element(s) or mirror(s) 23 as in FIG. 11. In FIG. 11, the camera's 20 viewing path has reference sign 25. The cameras 20 are used to detect the object 18, and/or to read a marking 24 on the object 18. The marking 24 may for instance be a bar code or an article number or similar. In particular, the cameras 20 are arranged such that no rotation of the object 18 is necessary to detect and/or read the marking 24.

Figure 1:
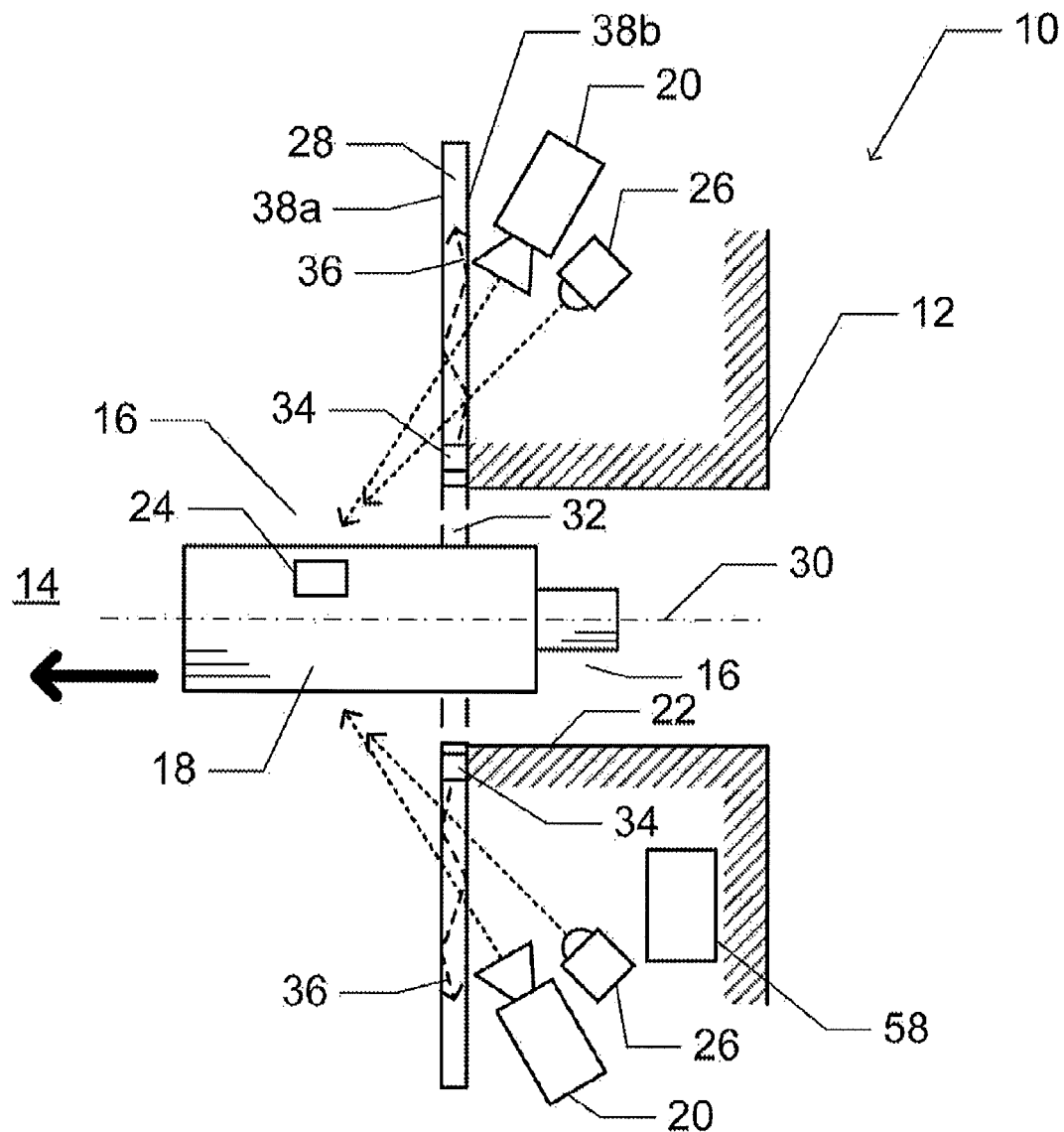
FIG. 1 is a schematic side view showing details of a reverse vending machine (RVM) according to one or more embodiments the present disclosure.

The RVM 10 may further comprise a plurality of lamps 26, typically one lamp 26 for each camera 20, for at least partly illuminating the object 18 in its position shown in FIG. 1. The lamps 26 facilitate or enable the detection/reading of the object 18/marking 24 by the cameras 20. The lamps 26 are not shown in FIG. 2 for the sake of clarity.

The RVM 10 further comprises a transparent or translucent plate 28. The plate 28 is preferably flat. The plate 28 is vertically arranged, and it is transversal to the longitudinal axis 30 of the chamber 16. The plate 28 is arranged after the cameras 20 as seen in the typical transportation direction of the object 18, and it has a first surface 38a facing away from the cameras 20 and a second surface 38b towards the cameras 20. Further, the plate 28 has a central opening 32 corresponding to the perimeter 22 of the chamber 16. The plate 28 is so arranged in relation to the cameras 20 that the cameras 20 in use view the object 18 obliquely through the plate 28, as best seen in FIG. 1. Preferably, the cameras 20 view the object 18 at an oblique angle in the range of 45-75° relative the axis 30. The plate 28 is generally provided for protecting the cameras 20 and the lamps 24 and other components from dirt. The plate 28 can for instance be made of glass or polymer glass.

During normal operation of the RVM 10, a user inserts returnable objects 18 from the front 12 into the chamber 16. Each object 18 is conveyed towards the back 14 of the RVM 10 to the position illustrated in FIG. 1 where the object 18 is illuminated by the lamps 26 and viewed by the cameras 20. Following the normal operation, dirt (e.g. liquids, solid matter, etc.) will inevitably stick to the exposed first surface 38a of the plate 28. The dirt typically comes from the returned objects 18, but it could also be a finger print, dust, etc. Eventually, the build-up of dirt may be so significant that it hampers the operation of the cameras 20. Namely, the cameras 20 get obscured by the dirt so that they cannot properly detect the object 18 or recognize the mark 24. Hence, the plate 28 must be cleaned.

Conveniently, the cameras 20 could be used for detecting if and optionally where dirt appears on the plate 28. However, the dirt is not readily visible for the cameras 20 using the "regular" lamps 26 due to the optical arrangement.

Figure 3A:
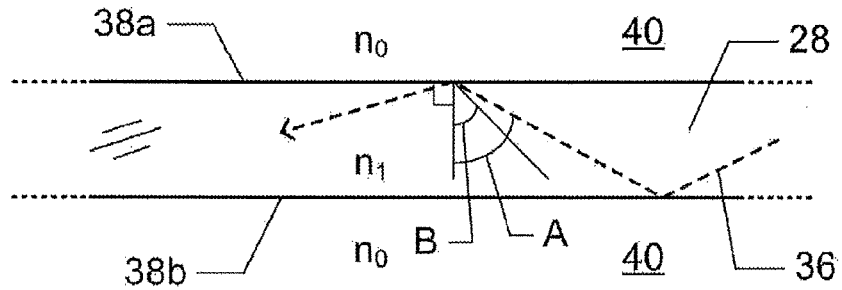
FIGS. 3*a-b* are side views showing TIR in a transparent or translucent plate without and with dirt.

To this end, the RVM 10 further comprises means 34 adapted to couple light 36 into the plate 28 such that the (in-coupled) light undergoes total internal reflection (TIR) in the plate 28, when the plate 28 is clean. Hence, the plate 28 may function as a wave guide. More specifically, the means 34 are arranged such that the in-coupled light 36 in the plate 28 travels at so acute angles relative the surfaces 38a and 38b that it strikes the surface 38a and 38b (which form an interface between the plate 28 and another medium 40 which usually—when the plate 28 is clean—is air) at an angle A of incidence with respect to said surfaces' normal greater than a critical angle B. This is illustrated in FIG. 3a. Air has a refraction index no=1. For a plate 28 made of glass with a refraction index ni=1.5, the critical angle B for TIR is 41.8°.

Figure 3B:
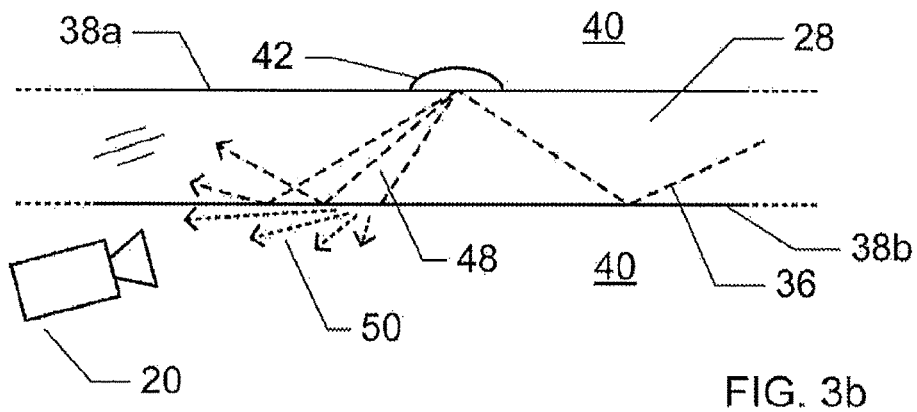
Figure 3C:
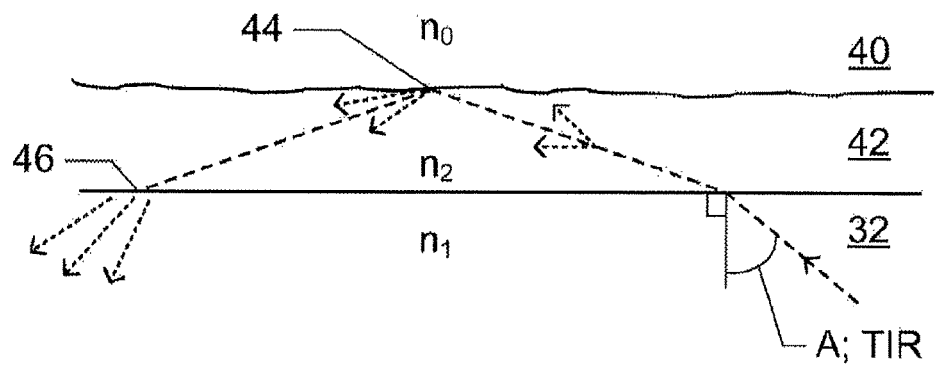
FIG. 3*c* is a partial enlarged view of FIG. 3*b*.

However, when dirt 42 appears on the first surface 38a of the plate 28, the condition for TIR may no longer be met at the area where the dirt 42 is, as further explained with reference to FIGS. 3b-3c.

At the plate-dirt interface, light 36 that with a clean plate 28 was subjected to TIR will now exit the plate 28 and enter the dirt 42, since the dirt 42 typically has a larger refraction index n2 than air. In the dirt 42, the light will be somewhat scattered, but most of the light will continue on towards the dirt-air interface 44. At the interface 44, the surface is typically a bit uneven. Also, the light goes from a higher refraction index n2 medium (dirt 42) towards a lower refraction index no medium (air 40), and the result is that total internal reflection occurs at interface 44. However, since the surface at interface 44 is uneven or irregular, it is believed that that the reflected light will again be somewhat scattered. And at the return into the plate 28 at 46, even more so-called forward scattering occurs.

A portion 48 of the scattered returned light travels at such angles that TIR is not fulfilled at the second surface 38b of the plate 28. Hence, this portion is coupled out from the plate 28 as indicated by reference sign 50 in FIG. 3b. The out-coupled light 50 is spread mainly parallel to the second surface 38b, and the amount of light gradually diminishes towards the normal of the second surface 38b. The out-coupled light parallel or almost parallel to the second surface 38b (or in other words: parallel or almost parallel to the plate 28) may be detected by the cameras 20. This allows the cameras 20 to clearly see the dirt 42 on the plate 28. Hence, no dedicated cameras or detector are needed to detect dirt in the present RVM 10. An exemplary camera 20 is schematically illustrated in FIG. 3b.

Figure 4:
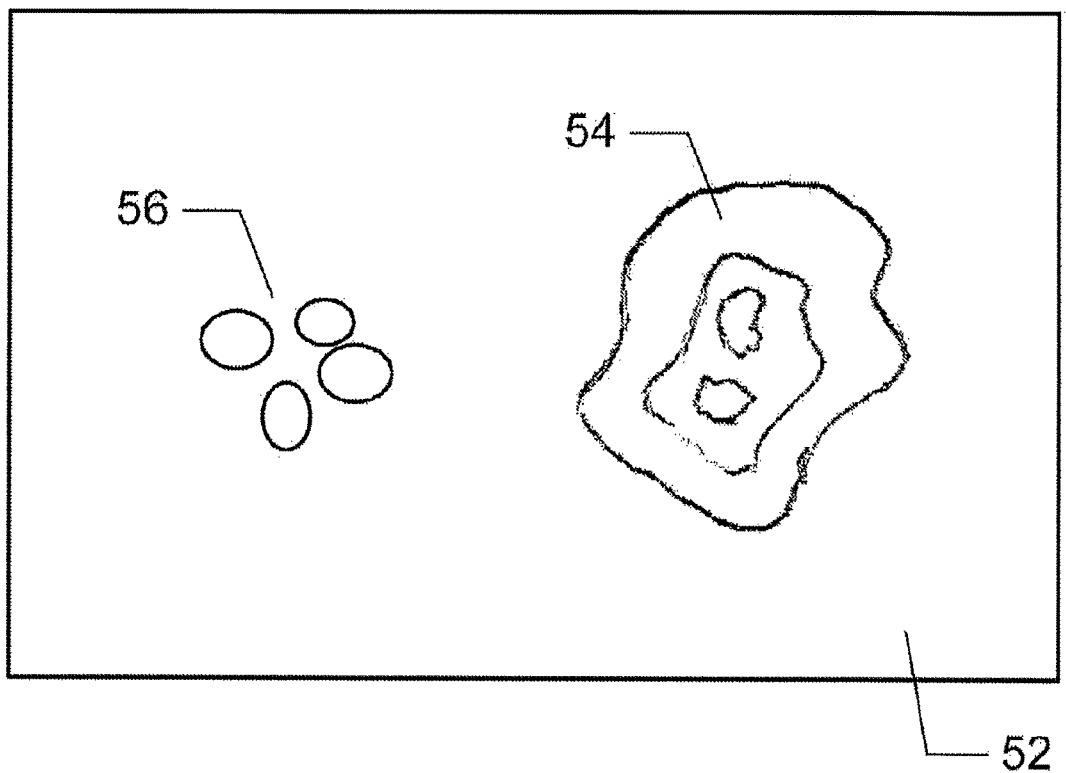
FIG. 4 is an exemplary image taken by a camera of the RVM.

To this end, a method of detecting dirt 42 in the reverse vending machine 10 in accordance with an embodiment of the present disclosure may comprise the steps of: manually or automatically activating the means 34 for coupling light 36 into the transparent or translucent plate 28; and viewing (or imaging) at least a portion or portions of the plate 28 using the cameras 20—while light 36 is coupled into the plate 28 using the means 34—for detecting any dirt 42 on the plate 28. Images from the cameras 20 clearly show any dirt 42 on the plate 28, and the images can be manually inspected by an operator or automatically analyzed by some computer means. The detection of dirt can be used to indicate that it is time to clean the plate 28, but it can also be used during the actual cleaning to see where the dirt is and/or to check after cleaning that the cleaning was successful. FIG. 4 is an image 52 taken by one of the cameras 20 when the means 34 are turned on, wherein the area 54 corresponds to dirt in the form of a finger print on the plate 28, and wherein the circles 56 correspond to dirt in the form of drops of water on the plate 28. Water drops on the plate are usually to some extent curved with respect to the plate's flat surface 38a, which makes them possible to detect. The images from the cameras 20 can be processed to more clearly show the dirt. For instance, at least one threshold could be used to indicate the strength(s) of the reflection. Also, several images from the same camera 20 could be superimposed or added together to increase the sensitivity.

The means 34 may be activated by an electronic controller 58 connected to the means 34 (connections between the controller 58 and means 34 are not shown in the drawings for the sake of clarity). Manual activation via the controller 58 may for instance be performed locally or remotely by an operator, while automatic activation can be performed in accordance with a preset maintenance time schedule, for example. Typically, all means 34 are activated at the same time.

Figure 2:
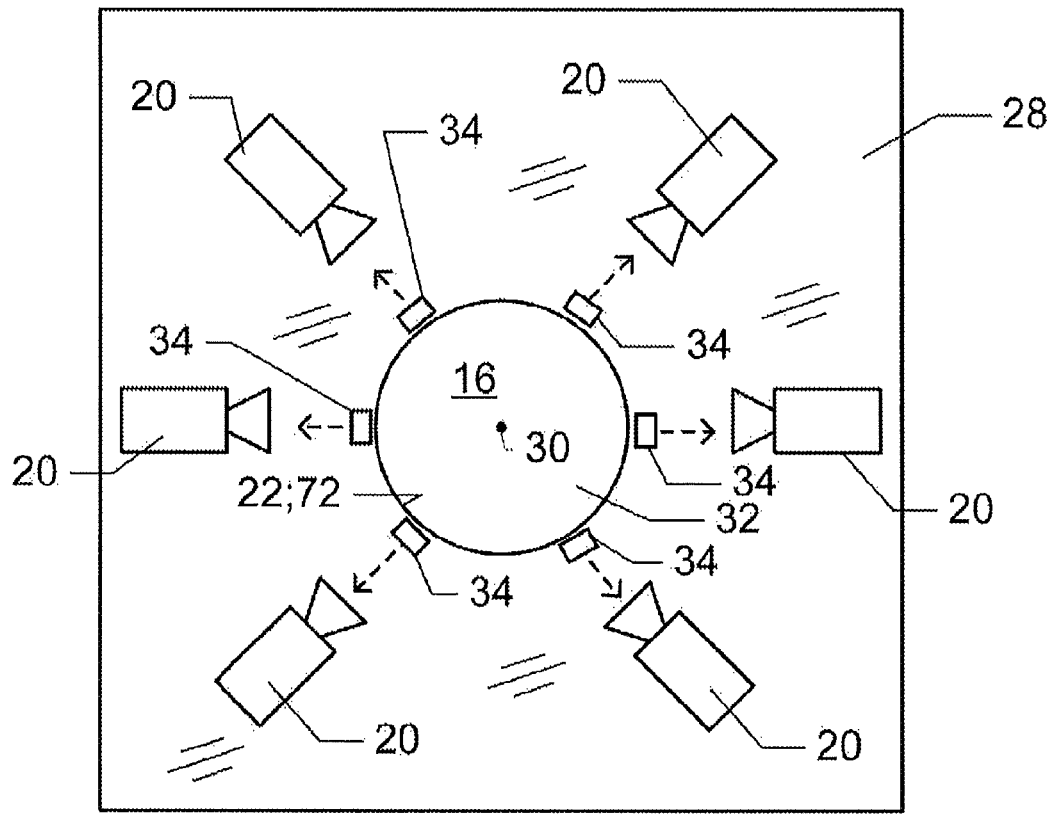
FIG. 2 schematically shows details of the RVM in FIG. 1 in front view.

The means 34 may be uniformly positioned around the opening 32, as seen best in FIG. 2. Typically, there is one means 34 for each camera 20. The means 34 are preferably placed at or near the edge 72 of the opening 32, so that they do not obstruct the cameras' 20 view of the object 18. Also, the means 34 may be arranged to couple light 36 into the plate 28 in directions that are generally opposite the viewing directions of the respective cameras 20 through the plate 28, namely in directions from the plate's opening 32 towards the outer perimeter of the plate 28, and in angular directions with respect to the axis 30 that correspond to the cameras' 20 angular positions about the axis 30. This ensures that any dirt 42 clearly appears in images recorded by cameras 20 (as mentioned above, the out-coupled light 50 is spread mainly parallel or almost parallel to the second surface 38b). Also, the means 34 are preferably provided on the same side of the transparent or translucent plate 28 as the cameras 20, i.e. opposite the exposed first surface 38a, so that they too can be protected by the plate 28.

Various exemplary means 34 for coupling light into the plate will now be described with reference to FIGS. 5-9. Typically, all means 34 in the RVM 10 are of the same type.

Figure 5:
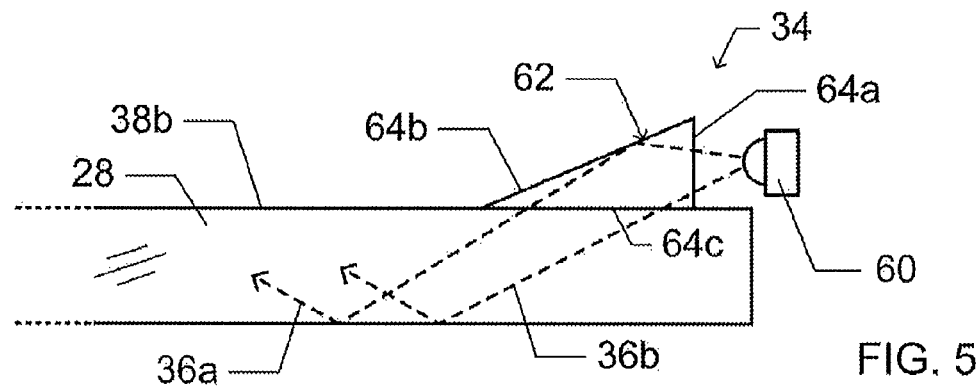
FIGS. 5-9 are side views showing various exemplary means for coupling light into the plate.

FIG. 5 is a side view of means 34 that includes a light source 60 and a prism 62. The prism 62 can be made of the same material as the plate 28, namely glass or polymer glass, for example. The prism 62 can be attached to the plate 28 e.g. by means of glue. The glue should have the same refractive index as the plate 28 and the prism 62. Also, the glue should be transparent to light. The prism 62 is a triangular prism with three rectangular surfaces 64a-64c. In FIG. 5, surfaces 64a and 64c are orthogonal, and surface 64c is attached to the plate 28. Further, the light source 60 is positioned in front of the surface 64a. In operation, light is emitted from the light source 50 towards and through surface 64a. Some light 36a is directly coupled into the plate 28 via surface 64c, while some light 36b is first reflected by the surface 64b before being coupled into the plate 28 via surface 64c.

Figure 6:
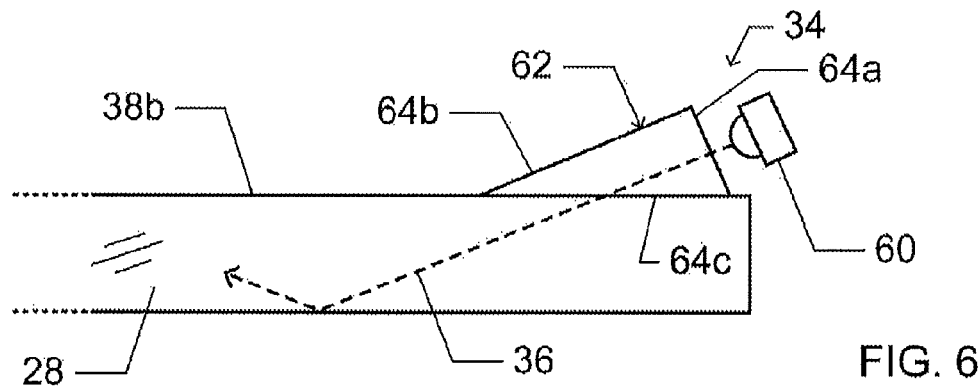

The means 34 in FIG. 6 is similar to that of FIG. 5, but the right angle is between surface 64a and surface 64b of the triangular prism 60. Also, the light source 60 is directed so that its main light emitting direction (illustrated by light 36 in FIG. 6) is orthogonal to the surface 64a.

The means 34 shown in FIGS. 5 and 6 are both efficient when it comes to coupling light into the plate 28.

Figure 7:
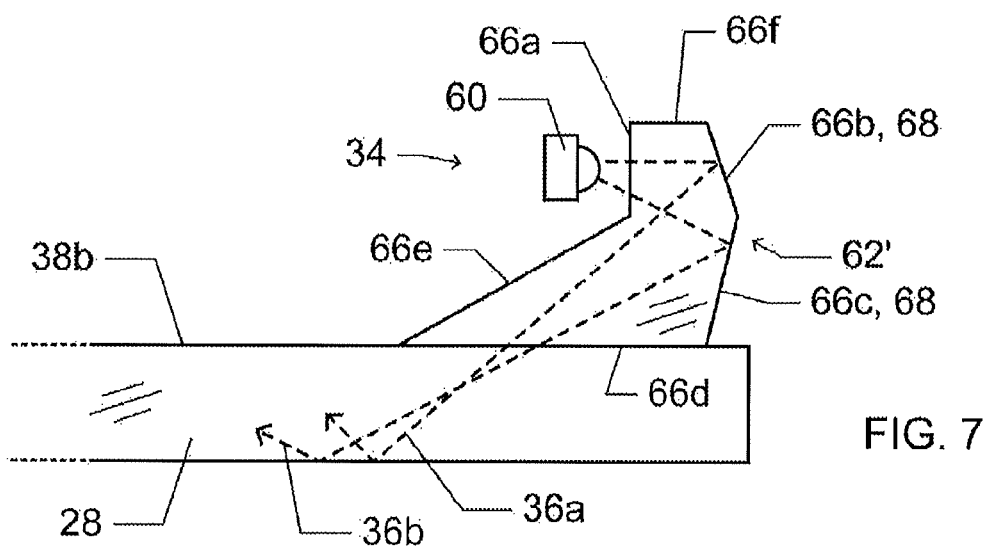
Figure 10:
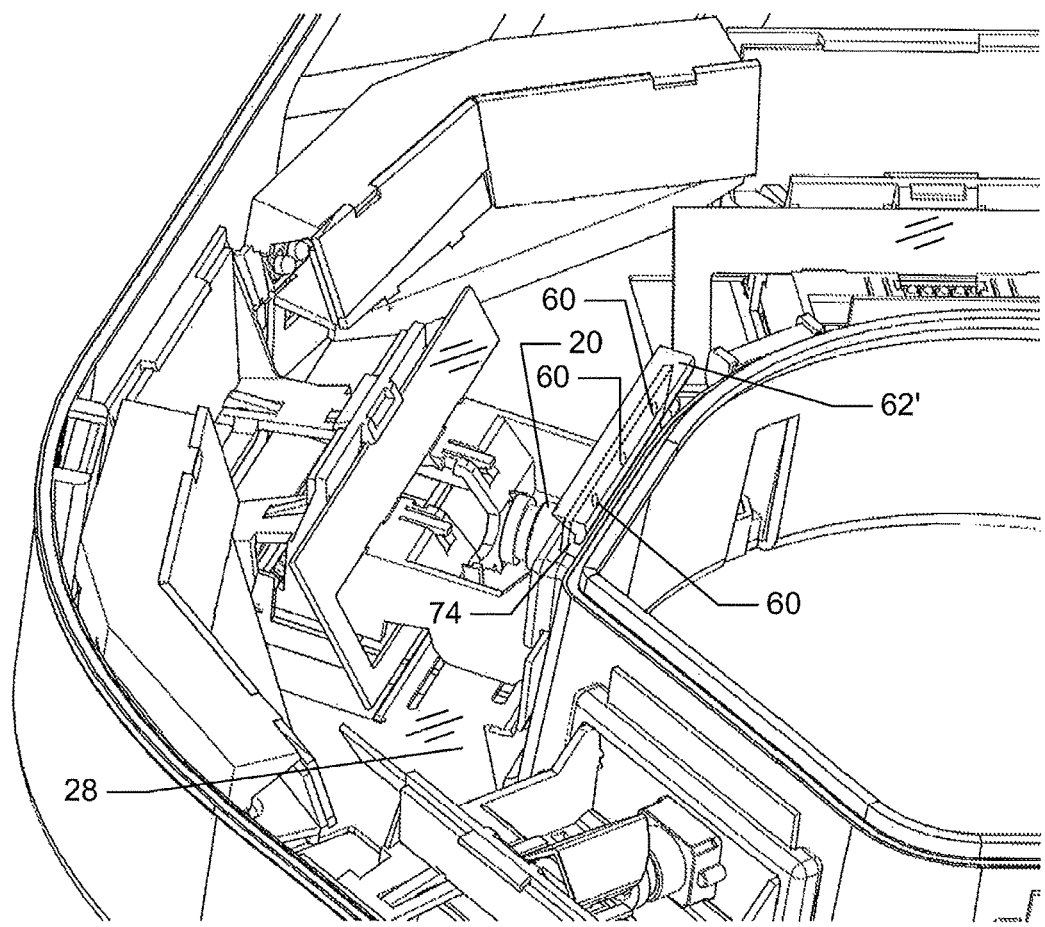
FIG. 10 is a partial perspective view of the RVM according to an embodiment of the present disclosure.
Figure 12:
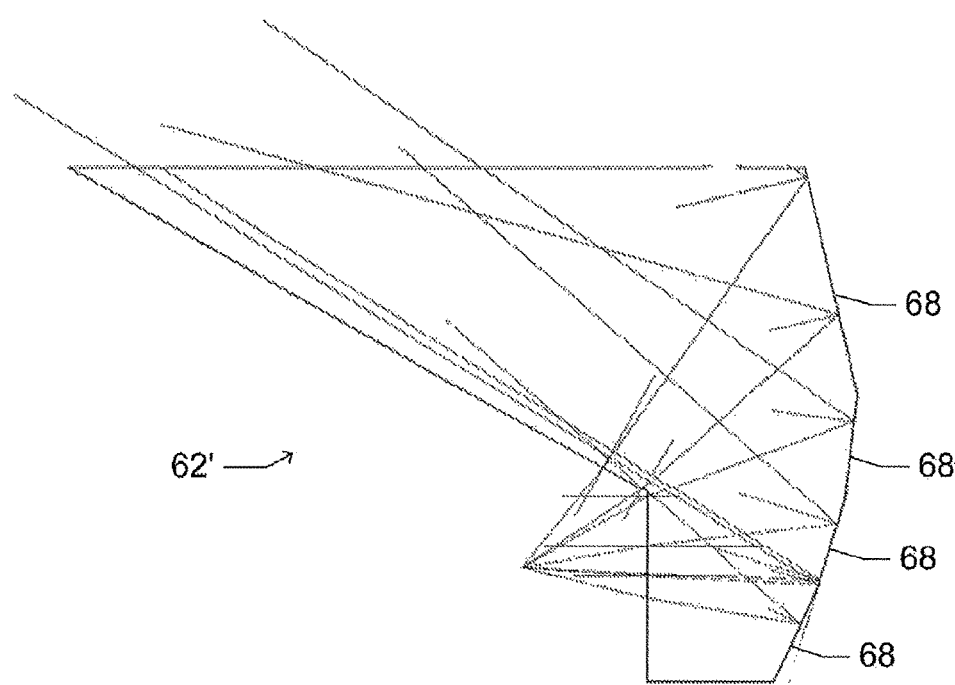
FIG. 12 is a side view of a prism according to an embodiment of the present disclosure.

The means 34 in FIG. 7 comprises a light source 60 and a prism 62'. The prism 62' comprises a first surface 66a for receiving light from the light source 60, two second surfaces 66b and 66c which are reflective, and a third surface 66d on the plate 28. The prism 62' further comprises a fourth surface 66e joining the surfaces 66a and 66d, and a fifth surface 66f joining the surfaces 66a and 66b. Generally, the two second surface 66b and 66c are arranged to receive light 36 in-coupled through the first surface 66a and reflect it towards the third surface 66c. The two second reflective surfaces 66b and 66c may for instance be provided with a reflective coating 68. A cross section of the prism 62' as seen in FIG. 7 may clockwise be defined by a line (66d) parallel to the surface 38b of the plate 28, a line (66e) forming an acute angle with line (66d), a line (66a) substantially orthogonal to the surface 38b, a line (66f) orthogonal to line (66a), a line (66b) forming a slightly blunt angle with line (66f), and a line (66c) forming an almost 180 degree angle with line (66b). The light source 60 is placed in front of the first surface 66a and is directed so that its main light emitting direction (illustrated by light 36a in FIG. 7) is orthogonal to the surface 66a. In operation, some light 36a is reflected by the reflective surface 66b into the plate 28 via surface 66d, while some light is reflected by the reflective surface 66c into the plate 28 via surface 66d. The means 34 in FIG. 7 may be more compact than the means 34 in FIGS. 5 and 6. The prism 62' is also shown in FIG. 10. An alternative embodiment of the prism 62' is shown in FIG. 12, with four reflective "second" surfaces.

Figure 8:
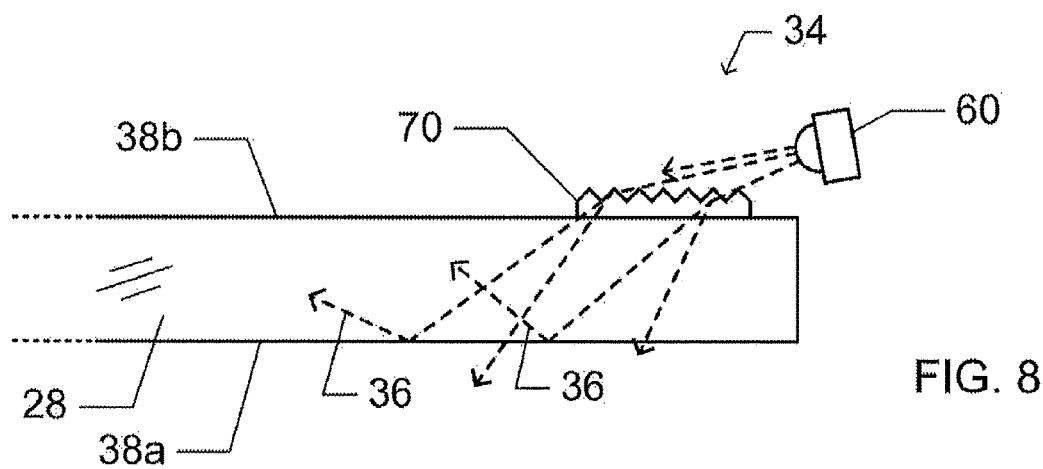

In FIG. 8, the means 34 includes a light source 60 and a diffuser 70, wherein the diffuser 70 is attached to the plate 28. The diffuser 70 may for instance be a holographic diffuser. A holographic diffuser known per se can have a controlled known scattering angle at least in the range of 10°-90°. The light source 60 may in this embodiment placed with its main light emitting direction parallel or almost parallel to the second surface 38b of the plate 28, to achieve sufficient in-coupling of light. The means 34 in FIG. 8 may be very compact.

Figure 9:
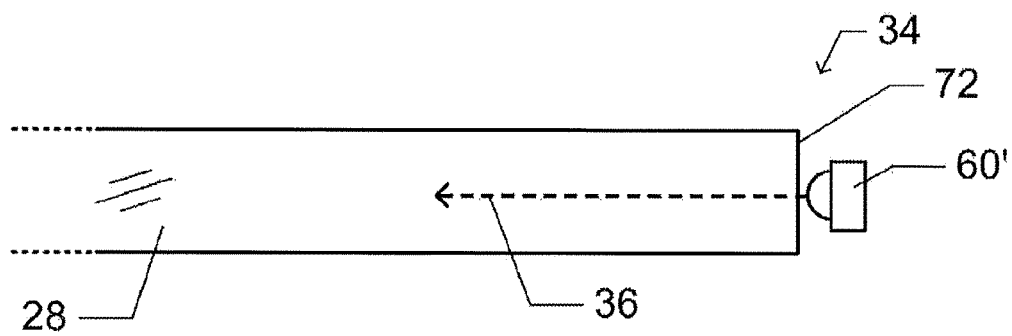

In FIG. 9, the means 34 includes at least one light source 60' arranged at the edge 72 of the plate 28. The edge 72 is towards the opening 32. In operation, the at least one light source 46' emits light 36 into the edge 72 of the plate 28 in directions that are substantially parallel to the plate's surfaces 38a and 38b, or at least with sufficiently small angles with respect to the surfaces 38a and 38b that TIR is achieved. This embodiment requires no prisms or similar elements for coupling in light into the plate 28.

A common feature of the various means 34 of FIGS. 5-9 is that they are external to the plate 28 and do not require any foreign element to be mounted into the plate 28, which may facilitate manufacturing. However, solutions which include elements in the plate 28 are also envisaged. For instance, the at least one light source 60' in FIG. 9 could be mounted in the edge 72 or inside the plate 28. Also, mirror elements angled at 45 degrees could be mounted inside the plate 28 for directing light entering the plate normal to the plate's 28 surfaces 38a and 38b in directions substantially parallel to the surfaces 38a and 38b, for example. Also, the diffuser of FIG. 8 could be embodied as etchings in the surface 38b of the plate 28.

The light sources 60, 60' may be adapted to emit pulsing red light when the means 34 are activated, but other types of light can be used as well. Also, the light sources 60, 60' may conveniently be mounted on the same circuit board 74 as the cameras 20 and the lamps 26 (see FIG. 10). Also, the light sources 60, 60' may for instance be LEDs (light emitting diodes).

The person skilled in the art will realize that the present disclosure by no means is limited to the embodiments described above. On the contrary, many modifications and variations are possible within the scope of the appended claims.

The invention claimed is:

1. A reverse vending machine, comprising:
   an interior adapted to receive an object returned to the reverse vending machine;
   a plurality of cameras arranged around the perimeter of the interior for viewing said object;
   a transparent or translucent plate arranged such that the cameras in use view the object obliquely through the transparent or translucent plate, wherein the transparent or translucent plate has an opening corresponding to the perimeter of the interior; and
   means adapted to couple light into the plate such that the light undergoes total internal reflection in the plate when the plate is clean,
   wherein said means are arranged to couple light into the plate in directions that are generally opposite the respective cameras' viewing directions through the plate, wherein said means are positioned around said opening, at or near the edge of the opening, and wherein said cameras are configured to detect any dirt or other obscuring matter on the plate when said means are activated.

2. A reverse vending machine according to claim 1, wherein said means are provided externally to the transparent or translucent plate.

3. A reverse vending machine according to claim 1, wherein said means are provided on the same side of the transparent or translucent plate as the cameras.

4. A reverse vending machine according to claim 1, wherein said means include at least one light source with an associated prism.

5. A reverse vending machine according to claim 4, wherein the prism is on the transparent or translucent plate, and wherein the light source is adapted to emit light that in use is coupled into the transparent or translucent plate via the associated prism.

6. A reverse vending machine according to claim 5, wherein the prism is triangular.

7. A reverse vending machine according to claim 5, wherein the prism has a first surface for receiving light from the light source, at least one second surface which is reflective, and a third surface facing the plate, and wherein the at least one second surface is arranged to receive light in-coupled through the first surface and reflect it towards the third surface.

8. A reverse vending machine according to claim 4, wherein the prism is triangular.

9. A reverse vending machine according to claim 4, wherein the prism has a first surface for receiving light from the light source, at least one second surface which is reflective, and a third surface facing the plate, and wherein the at least one second surface is arranged to receive light in-coupled through the first surface and reflect it towards the third surface.

10. A reverse vending machine according to claim 1, wherein said means include at least one light source with an associated diffuser which is on the transparent or translucent plate.

11. A reverse vending machine according to claim 1, wherein said means include one or more light sources arranged at an edge of the transparent or translucent plate for directing light into the edge of the plate.

12. A reverse vending machine according to claim 1, further comprising a controller connected to said means for manual and/or automatic activation of said means.

13. A method of detecting dirt or other obscuring matter in a reverse vending machine as defined in claim 1, which method comprises:
   manually or automatically activating said means for coupling light into the transparent or translucent plate; and
   viewing at least a portion or portions of said plate using said cameras while light is coupled into the plate using said means for detecting any dirt or other obscuring matter on said plate.

14. A reverse vending machine, comprising:
   an interior adapted to receive an object returned to the reverse vending machine;
   a plurality of cameras arranged around the perimeter of the interior for viewing said object;
   a transparent or translucent plate arranged such that the cameras in use view the object obliquely through the transparent or translucent plate, wherein the transparent or translucent plate has an opening corresponding to the perimeter of the interior; and
   means adapted to couple light into the plate such that the light undergoes total internal reflection in the plate when the plate is clean,
   wherein said means are arranged to couple light into the plate in directions that are generally opposite the respective cameras' viewing directions through the plate, and wherein said cameras are configured to detect any dirt or other obscuring matter on the plate when said means are activated.

* * * * *